United States Patent [19]

Hunger et al.

[11] 3,937,834

[45] Feb. 10, 1976

[54] PHARMACEUTICAL PREPARATIONS

[75] Inventors: Alfred Hunger, Basel; Hans-Jochen Janssen, Riehen, both of Switzerland

[73] Assignee: Ciba-Geigy Corporation, Ardsley, N.Y.

[22] Filed: Nov. 19, 1973

[21] Appl. No.: 417,305

Related U.S. Application Data

[63] Continuation-in-part of Ser. No. 180,492, Sept. 14, 1971, abandoned.

[30] Foreign Application Priority Data

Oct. 2, 1970 Switzerland.................... 14614/70

[52] U.S. Cl................................. 424/273; 424/330
[51] Int. Cl.² ............. A61K 31/175; A61K 31/415
[58] Field of Search.......................... 424/273, 330

[56] References Cited
FOREIGN PATENTS OR APPLICATIONS

| | | |
|---|---|---|
| 1,184,827 | 3/1970 | United Kingdom |
| 1,187,546 | 4/1970 | United Kingdom |
| 1,194,548 | 6/1970 | United Kingdom |
| 1,201,460 | 8/1970 | United Kingdom |
| 1,206,420 | 9/1970 | United Kingdom |

OTHER PUBLICATIONS

Chem. Abst. (1) Vol. 65 – 12509e (1966).

Chem. Abst. (2), Vol. 74 – 74616e (1971).

Chem. Abst. (3), Vol. 73 – 120315k (1970).

*Primary Examiner*—Stanley J. Friedman
*Attorney, Agent, or Firm*—Joseph G. Kolodny; John J. Maitner; Theodore O. Groeger

[57] ABSTRACT

The present invention relates to new pharmaceutical compositions comprising an α-receptor blocker, a β-receptor blocker and a pharmaceutical carrier and to a method of using said compositions in the treatment of high blood pressure and angina pectoris.

3 Claims, No Drawings

PHARMACEUTICAL PREPARATIONS

CROSS-REFERENCES TO RELATED APPLICATION

This is a continuation-in-part application of our copending application Ser. No. 180,492, filed Sept. 14, 1971, now abandoned.

The invention relates to new pharmaceutical preparations which contain as active substances a β-receptor blocker and an α-receptor blocker. These pharmaceutical preparations are particularly suitable for treating high blood pressure and angina pectoris in warm-blooded animals.

By treating angina pectoris with β-blockers, the intention is to avoid excessive stimulation of the heart by inhibiting the sympathomimetic amines, adrenalin and noradrenalin. Simultaneously, however, the basically vasodilative action of adrenalin and noradrenalin, which occur as chemical carrier substances in the sympathetic nervous system, is reversed to cause a vasoconstrictive action. Increased heart activity, which is undesirable in the case of angina pectoris results therefrom.

Furthermore, in the treatment of high blood pressure with an α-receptor blocker, which produces a peripheral vasodilatation, the sympathetic nervous system is reflexly activated. Rapid heart action (tachycardia etc.) results which causes distress and counteracts vasodilatation, so that only an insufficient lowering of pressure results.

The above mentioned side effects are very largely eliminated by the preparations according to the invention.

Suitable β-blockers are in particular compounds of the formula

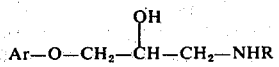

in which Ar represents an isocyclic, homocyclic or heterocyclic radical which contains at least one six-membered aromatic ring (preferably a phenyl, naphthyl, tetralyl, indolyl, or indanyl radical) and which is bonded directly with the radical of the molecule and can be substituted by one more lower alkyl, alkoxy, alkenyl, alkenyloxy, aklinyl, alkinyloxy, alkylmercapto, alkylsulphonyl, hydroxyalkyl, aminoalkyl, alkylamino, dialkylamino, alkanoyl, alkanoyloxy, benzamido, or alkanoylamino radicals, aryl, aryloxy, arylamino, arylmercapto, arylsulphonyl, arylsulphonylamino, arylamino, aryl-lower alkoxy, lower halogen-alkyl, alkoxyalkyl, monoalkylaminoalkyl, or dialkylaminoalkyl radicals, nitro, hydroxy, amino, and/or, cyano groups and/or halogen atoms, and R represents a lower, especially a branched, alkyl or hydroxyalkyl radical, primarily the tert. butyl, sec. butyl, or preferably the isopropyl radical.

In the above mentioned substituents of the radical Ar are lower alkyl radicals chiefly those containing at least 6 carbon atoms, for example methyl, ethyl, propyl, isopropyl, straight or branched butyl, pentyl or hexyl radicals bonded in any desired position.

Lower alkenyl radicals are, for example, those containing at most 6 carbon atoms, especially allyl or methallyl radicals. A suitable lower alkinyl radical is preferably the propargyl radical. Examples of alkanoyl radicals are primarily propionyl or butyryl radicals, preferably, however, the acetyl radical. Aryl radicals are primarily naphthyl radicals, or especially phenyl radicals. Halogen atoms are especially fluorine or chlorine atoms.

A preferred group of β-blockers are the compounds of formula I, wherein R has the meanings as indicated and Ar represents a phenyl radical substituted by an unsaturated radical, for example a lower alkenyl, alkinyl, alkenyloxy, alkinyloxy, or cyano group, and compounds of formula I, wherein R has the meanings indicated and Ar represents a phenyl radical substituted by a lower hydroxyalkyl, alkanoylamino, or mercaptoalkyl group.

β-Blockers that may be specially mentioned are: 1-(1-naphthyloxy)-2-hydroxy-3-isopropylaminopropane, 1-(3-tolyloxy)-2-hydroxy-3-isopropylaminopropane, 1-(3,5-xylyloxy)-2-hydroxy-3-isopropylaminopropane, 1-(2-cyano-3-methyl phenoxy)-2-hydroxy-3-isopropylaminopropane, 1-(2-methylmercaptophenoxy)-2-hydroxy-3-isopropylaminopropane, 1-(2-allylphenoxy)-2-hydroxy-3-isopropylaminopropane, 1-(4-acetamidophenoxy)-2-hydroxy-3-isopropylaminopropane, 1-(2-allyloxyphenoxy)-2-hydroxy-3-isopropylaminopropane, 1-(4-methansulfonylamidophenoxy)-2-hydroxy-3-isopropylaminopropane, 1-(5,6,7,8-tetrahydro-1-naphtoxy)-2-hydroxy-3-isopropylaminopropane, 1-(4-Benzamidophenoxy)-2-hydroxy-3-isopropylaminopropane, 1-(4-Indanyloxy)-2-hydroxy-3-isopropylaminopropane, 1-(2-bromophenoxy)-2-hydroxy-3-isopropylaminopropane, 1-(4-cyanophenoxy)-2-hydroxy-3-isopropylaminopropane, 1-(2-cyanophenoxy)-2-hydroxy-3-isopropylaminopropane, 1-(2-ethinylphenoxy)-2-hydroxy-3-isopropylaminopropane, 1-(2-methoxymethylphenoxy)-2-hydroxy-3-isopropylaminopropane, 1-(2-hydroxymethylphenoxy)-2-hydroxy-3-isopropylaminopropane, 1-(2-propargyloxyphenoxy)-2-hydroxy-3-isopropylaminopropane, 1-(2-methoxyphenoxy)-2-hydroxy-3-isopropylaminopropane, 1-(2-isopropoxyphenoxy)-2-hydroxy-3-isopropylaminopropane, 1-(2-methallyloxyphenoxy)-2-hydroxy-3-isopropylaminopropane, 1-(4-indolyloxy)-2-hydroxy-3-isopropylaminopropane, 1-(2-phenylphenoxy)-2-hydroxy-3-isopropylaminopropane, 1-(2-phenoxyphenoxy)-2-hydroxy-3-isopropylaminopropane, 1-(2-chloro-5-methylphenoxy)-2-hydroxy-3-tert.-butylaminopropane, 1-(2-cyanophenoxy)-2-hydroxy-3-tert.-butylaminopropane, 1-(2-ethinylphenoxy)-2-hydroxy-3-tert.-butylaminopropane, 1-(2-allylphenoxy)-2-hydroxy-3-tert.-butylaminopropane, 1-(2-phenylphenoxy)-2-hydroxy-3-tert.-butylaminopropane, 1-(2-methoxymethylphenoxy)-2-hydroxy-3-tert.-butylaminopropane, 1-(4-acetamidophenoxy)-2-hydroxy-3-tert.-butylaminopropane, 1-(2-hydroxymethylphenoxy)-2-hydroxy-3-tert.-butylaminopropane, 1-(2-allyloxyphenoxy)-2-hydroxy-3-tert.-butylaminopropane, 1-(2-cyanophenoxy)-2-hydroxy-3-tert.-pentylaminopropane, 1-(4-allyloxyphenoxy)-2-hydroxy-3-isopropylaminopropane, 1-(4-methallyloxyphenoxy)-2-hydroxy-3-isopropylaminopropane, 1-(4-propargyloxyphenoxy)-2-hydroxy-3-isopropylaminopropane, 1-(4-allyloxyphenoxy)-2-hydroxy-3-tert.-butylaminopropane, 1-(2-methoxyphenoxy)-2-hydroxy-3-tert.-pentylaminopropane and 1-(2-methoxyphenoxy)-2-hydroxy-3-(1,1-dimethylbutyl)-aminopropane.

Further examples of β-blockers that may be considered are those of the formula

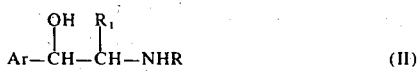
(II)

wherein Ar represents a phenyl, naphthyl, tetralyl, or indanyl radical, which can also be substituted by lipophil substituents, for example halogen atoms, nitro groups, lower alkyl and/or alkoxy radicals, R denotes a lower, preferably a branched, hydroxyalkyl or alkyl radical, and $R_1$ represents a hydrogen atom or a lower alkyl radical. Preferred compounds of this group are: 1-(3,4-dichlorophenyl)-1-hydroxy-2-isopropylaminoethane (dichloroisoproterenol), 1-(1'-naphthyl)-1-hydroxy-2-isopropylaminoethane (Pronethalol), 1-(2,5-dimethoxyphenyl)-1-hydroxy-2-methyl-2tert.-butylaminoethane, 1-(4-methansulfonylaminophenyl)-1-hydroxy-2-isopropylaminoethane, 1-(5,6,7,8-tetrahydro-1-naphthyl)-1-hydroxy-2-sec.-butylaminoethane and 1-(4-nitrophenyl)-1-hydroxy-2-isopropylaminopropane.

Suitable α-blockers are any sympatholytically active compounds such, for example, as dihydroergot alkaloids, such as dihydroergotamine, dihydroergocornine, dihydroergocristine or dihydroergocryptine, 2-benzyl-2-imidazoline, N-(2-chloroethyl)-N-(1-methyl-2-phenoxyethyl)-benzylamine, 2-(piperidinomethyl)-1,4-benzodioxan, 6-allyl-6,7-dihydro-5H-dibenz[c,e]azepine, 1,4-bis-(1,4-benzodioxan-2-ylmethyl)-piperazine, N-(2-chloroethyl)-dibenzylamine, and primarily 2-[N-(m-hydroxyphenyl)-p-toluidinomethyl]-2-imidazoline.

The α- and β-blockers mentioned hereinabove may be present in the form of isomer mixtures, pure isomers (racemates), or optical antipodes, according to the number of their asymmetric carbon atoms. They are used preferably in each case in the form of the more effective or less toxic isomers or antipodes.

The cited α- and β-blockers furthermore may be in the free form or in the form of their non-toxic salts. As non-toxic salts there may be considered especially salts with organic or inorganic acids such, for example, as: hydrohalic acids, sulphuric acids, phosphoric acids, nitric acids, perchloric acids, aliphatic, alicyclic, aromatic or heterocyclic carboxylic or sulphonic acids, for example formic, acetic, propionic, succinic, glycolic, lactic, malic, tartaric, citric, ascorbic, maleic, hydroxymaleic, or pyruvic acid; also phenylacetic, benzoic, p-aminobenzoic, anthranilic, p-hydroxybenzoic, salicylic or p-aminosalicylic acid, embonic acid, methanesulphonic, ethanesulphonic, hydroxyethanesulphonic and ethylenesulphonic acid; furthermore, halobenzenesulphonic, toluenesulphonic, naphthalenesulphonic acid or sulphanilic acid; as well as cyclohexyl-sulphamic acid, methionine, tryptophane, lysine, or argenine.

The invention relates therefore to pharmaceutical preparations which contain a β-blocker, especially one of those mentioned hereinabove, together with an α-blocker, especially one of those mentioned hereinabove, and to the manufacture of these preparations and furthermore to the application of these active substances in the form of the said preparations for the treatment of high blood pressure or of angina pectoris.

Of quite especial value are pharmaceutical preparations that contain as β-blocker: 1-(1-naphthyloxy)-2-hydroxy-3-isopropylamino-propane, 1-(3-tolyloxy)-2-hydroxy-3-isopropylamino-propane, 1-(2-allylphenoxy)-2-hydroxy-3-isopropylamino-propane, 1-(4-acetamidophenoxy)-2-hydroxy-3-isopropylamino-propane, or above all, 1-(2-allyloxyphenoxy)-2-hydroxy-3-isopropylamino-propane, or 1-(4-allyloxyphenoxy)-2-hydroxy-3-isopropylamino-propane, and as α-blocker one of the α-blockers mentioned above, above all 2-[N-(m-hydroxyphenyl)-p-toluidinomethyl]-2-imidazoline.

The invention is thus very particularly concerned with preparations which contain 1-(2-allyloxyphenoxy)-2-hydroxy-3-isopropylaminopropane or 1-(4-allyloxyphenoxy)-2-hydroxy-3-isopropylaminopropane together with 2-[N-(m-hydroxyphenyl)-p-toluidinomethyl]-2-imidazoline.

Accordingly, the use of these preferred preparations is also a special feature of the invention.

The ratio of β-blocker to α-blocker may vary within wide limits in the new preparations. The dosage of the new preparations naturally depends upon the effectiveness of the α- and β-blockers concerned and the individual needs of the patient. In the case of the β-blocking component, for example, it may lie in the range between the simple individual dose and double the individual dose; but preferably the simple individual dose is used. Thus, for example, the particularly preferred preparations mentioned above may contain 40 to 80 mg, especially 40 mg, of 1-(2-allyloxyphenoxy)-2-hydroxy-3-isopropylaminopropane hydrochloride or 100 to 200 mg, especially 100 mg, of 1-(4-allyloxyphenoxy)-2-hydroxy-3-isopropylaminopropane hydrochloride, respectively. The dosage of the α-blocking component may lie between the simple individual dose and a dose 2½ times the individual dose; but preferably the simple individual dose is used. Thus, for example, the preferred preparations just mentioned may contain 20 to 50 mg, especially 20 mg, of 2-[N-(m-hydroxyphenyl)-p-toluidinomethyl]-2-imidazoline hydrochloride.

In general, the ratio of the β-blocking to the α-blocking component is preferably from 5 to 1 up to 1 to 40, most preferably from 2 to 1 up to 1 to 30.

The pharmaceutical preparations of the invention are particularly suitable for oral application and may contain the usual carriers such, for example, as lactose, starch, gelatine, colloidal silica, magnesium stearate, talc, phenylvinylpyrrolidone, and similar substances. They can furthermore be combined with other therapeutically valuable substances. They are available for example, in the form of tablets, dragees, or capsules. They are obtained in the usual way. For a rectal application the pharmaceutical preparations are especially in the form of suppositories, that are obtained in the usual way.

The α-blockers and β-blockers used are known or can be manufactured in a manner known per se.

The following Examples illustrate the invention, without thereby in any way limiting the scope thereof.

EXAMPLE 1

Tablets containing 40 mg of 1-(2-allyloxyphenoxy)-2-hydroxy-3-isopropylaminopropane-hydrochloride (racemate) and 20 mg of 2-[N-(m-hydroxyphenyl)-p-toluidinomethyl]-2-imidazoline-hydrochloride can be manufactured from, for example, the following ingredients:

Composition

| | |
|---|---|
| 1-(2-allyloxyphenoxy)-2-hydroxy-3-isopropylaminopropane-hydrochloride | 40 mg |
| 2-[N-(m-hydroxyphenyl)-p-toluidino= | |

-continued

| Composition | |
|---|---|
| methyl]-2-imidazoline-hydrochloride | 20 mg |
| Lactose | 113 mg |
| Wheat starch | 90 mg |
| Colloidal silica | 10 mg |
| Polyvinyl pyrrolidone | 10 mg |
| Talcum | 15 mg |
| Magnesium stearate | 2 mg |
| | 300 mg |

Manufacture

The two active substances are mixed with the lactose, the colloidal silica and a part of the wheat starch. The mixture is passed through a sieve and kneaded with an aqueous-alcoholic solution of polyvinylpyrrolidone until a plastic mass is obtained. This mass is forced through a sieve, dried and the dry granulate again passed through a sieve. The remaining wheat starch, talc and magnesium stearate are then admixed and the resulting mixture compressed into tablets of 300 mg each with dividing groove.

The dose is 1 tablet 3 times daily to a maximum of 2 tablets 4 times daily.

EXAMPLE 2

Tablets containing 20 mg of -(-)-1-(2-allyloxyphenoxy)-2-hydroxy-3-isopropylaminopropane-hydrochloride and 20 mg of 2-[N-(m-hydroxyphenyl)-p-toluidinomethyl]-2-imidazoline-hydrochloride can be manufactured from, for example, the following ingredients:

| Composition | |
|---|---|
| 1-(-)-1-(2-allyloxyphenoxy)-2-hydroxy-3-isopropylaminopropane-hydrochloride | 20 mg |
| 2-[N-(m-hydroxyphenyl)-p-toluidinomethyl]-2-imidazoline-hydrochloride | 20 mg |
| Lactose | 47 mg |
| Wheat starch | 45 mg |
| Colloidal silica | 5 mg |
| Polyvinyl pyrrolidone | 5 mg |
| Talcum | 7 mg |
| Magnesium stearate | 1 mg |
| | 150 mg |

Manufacture

The two active substances are mixed with the lactose, the colloidal silica and a part of the wheat starch. The mixture is passed through a sieve and kneaded with an aqueous-alcoholic solution of polyvinylpyrrolidone until a plastic mass is obtained. This mass is forced through a sieve, dried and the dry granulate again passed through a sieve. The remaining wheat starch, talc and magnesium stearate are then admixed and the resulting mixture compressed into tablets of 150 mg each with dividing groove.

The dose is 1 tablet 3 times daily to a maximum of 2 tablets 4 times daily.

EXAMPLE 3

Tablets containing 100 mg of 1-(4-allyloxyphenoxy)-2-hydroxy-3-isopropylaminopropane-hydrochloride and 20 mg of 2-[N-(m-hydroxyphenyl)-p-toluidinomethyl]-2-imidazoline-hydrochloride can be manufactured from, for example, the following ingredients:

| Composition | |
|---|---|
| 1-(4-allyloxyphenoxy)-2-hydroxy-3-isopropylaminopropane-hydrochloride | 100 mg |
| 2-[N-(m-hydroxyphenyl)-p-toluidinomethyl]-2-imidazoline-hydrochloride | 20 mg |
| Lactose | 232 mg |
| Wheat starch | 180 mg |
| Colloidal silica | 15 mg |
| Polyvinyl pyrrolidone | 20 mg |
| Talcum | 28 mg |
| Magnesium stearate | 5 mg |
| | 600 mg |

Manufacture

The two active substances are mixed with the lactose, the colloidal silica and a part of the wheat starch. The mixture is passed through a sieve and kneaded with an aqueous-alcoholic solution of polyvinylpyrrolidone until a plastic mass is obtained. This mass is forced through a sieve, dried and the dry granulate again passed through a sieve. The remaining wheat starch, talc and magnesium stearate are then admixed and the resulting mixture compressed into tablets of 600 mg each with dividing groove.

The dose is approx. 1 to 2 tablets 3 times daily.

We claim:

1. A pharmaceutical preparation for the treatment of angina pectoris and high blood pressure, containing a β-receptor blocker selected from the group consisting of 1-(2-allyloxyphenoxy)-2-hydroxy-3-isopropylaminopropane and 1-(4-indanyloxy)-2-hydroxy-3-isopropylaminopropane or a non-toxic salt thereof and an α-receptor blocker, 2-[N-(m-hydroxyphenyl)-p-toluidinomethyl]-2-imidazoline, or a non-toxic salt thereof together with a pharmacuetical carrier wherein the β-blocker and the α-blocker are in a ration of from 5 to 1 to 1 to 40.

2. A pharmaceutical preparation as claimed in claim 1, containing the β-blocker and the α-blocker in a ratio from 2 to 1 up to 1 to 30.

3. A pharmaceutical preparation for the treatment of angina pectoris and high blood pressure, containing effective amounts of a β-receptor blocker selected from the group consisting of 1-(2-allyloxyphenoxy)-2-hydroxy-3-isopropylaminopropane and 1-(4-indanyloxy)-2-hydroxy-3-isopropylaminopropane or a non-toxic salt thereof and an α-receptor blocker, 2-[N-(m-hydroxyphenyl)-p-toluidinomethyl]-2-imidazoline, or a non-toxic salt thereof together with a pharmaceutical carrier.

* * * * *